United States Patent [19]

Zemel et al.

[11] Patent Number: 5,420,237
[45] Date of Patent: May 30, 1995

[54] ENZYMATIC SYNTHESIS OF POLYANILINE

[75] Inventors: Haya Zemel, Wilmette; John F. Quinn, Arlington Heights, both of Ill.

[73] Assignee: AlliedSignal Inc., Morris Township, Morris County, N.J.

[21] Appl. No.: 91,456

[22] Filed: Jul. 14, 1993

Related U.S. Application Data

[63] Continuation of Ser. No. 751,948, Aug. 29, 1991, abandoned.

[51] Int. Cl.$^6$ .................. C08G 73/00; C08G 65/38
[52] U.S. Cl. ............................ 528/422; 528/38; 528/210; 524/555
[58] Field of Search ............ 524/555; 424/78.05; 528/422, 38, 210

[56] References Cited

U.S. PATENT DOCUMENTS

| | | | |
|---|---|---|---|
| 4,647,952 | 3/1987 | Pokora et al. | 435/256 |
| 4,886,625 | 12/1989 | Albarella et al. | 252/500 |
| 4,898,921 | 2/1990 | Humphrey et al. | 252/582 |
| 4,900,671 | 2/1990 | Pokora et al. | 435/256 |
| 5,143,828 | 9/1992 | Akkara et al. | 435/41 |

FOREIGN PATENT DOCUMENTS

PCT/US86/-
  02259  5/1987  WIPO .

OTHER PUBLICATIONS

Mann et al. Proceedings Royal Foriety vol. 119 pp. 47–60.
Aizawa et al. Journal of Biotechnology 14 1990 301–310.
Saunders, B. C., *Studies in Peroxidase Action-XVII\**, (Aug. 16, 1966).
Pandey, G., *Mushroom Tyrosnase Catalysed Coupling of Hindered Phenols: A Novel Approach for the Synthesis of Diphenoouinones and Disphenols*, (1990).
Sjoblad, R. D., *Polymerization of 1-Naphthol and Related Phenolic Compounds by an Extracellular Fungal Enzyme*, (Jan. 27, 1976).
Aizawa, Masuor, *Enzymatic Synthesis of Polyaniline Film Using a Copper-Containing Oxidoreductase: Bilibu-rin Oxidase*, (1989).
Duane, B. F. *Division S-3-Soil Microbiology and Biochemistry*, (1984).
Sjoblad, R. D., *Oxidative Coupling of Aromatic Compounds by Enzymes Soil Microorganism, in Soil Biochemistry*, Ch.3, vol. 5 (1981).
Booth, H., *Studies in Peroxidase Action, Part X\* The Oxidation of Phenols*, (1955).
Jonathan S. D., *Polymerization of Phenols Catalyzed by Peroxidase in Nonaqueous Media*, (1986).
Jonathan, D. S., *Enzymatic Catalysis in Monophasic Organic Solvents*, (1989).
Mann, P. J. G., *Studies in Peroxidase Action I-The Oxidation of Aniline*, (1935).
Shiro Kobayashi et al., "Enzymatic oxidation polymerization of o–phenylene" Chemistry Letters, pp. 393–394, 1992.
Chemical Abstracts, vol. 118, No. 2, Jan. 11, 1993, Abstract No. 7476y Akkara, J. A. et al. "Characterization of polyaniline synthesized by enzyme-catalyzed reactions in organic solvents".

*Primary Examiner*—Thurman K. Page
*Assistant Examiner*—Peter F. Kulkosky
*Attorney, Agent, or Firm*—Darryl L. Webster; Mary Jo Boldingh; Harold N. Wells

[57] ABSTRACT

This invention relates to a process for the enzymatic synthesis of electrically conductive substituted and unsubstituted polyanilines. Aniline monomer(s), an oxidizing agent, which comprises an enzyme and an electron acceptor, and an acidifying agent are reacted together to form polyanilines.

26 Claims, No Drawings

ENZYMATIC SYNTHESIS OF POLYANILINE

This application is a continuation of application Ser. No. 07/751,948, filed Aug. 29, 1991, now abandoned.

BACKGROUND OF THE INVENTION

1. Field of Invention

This invention relates to a process for the enzymatic synthesis of electrically conductive substituted or unsubstituted polyanilines, and to compositions comprising such polyanilines and other non-electrically conductive polymers. Another aspect of this invention relates to a method of using such polyanilines and compositions to form conducting polymer articles, including films, and to such articles.

2. Prior Art

In the field of conducting polymers there is a need to develop efficient methods of manufacture. The preferred chemical method of producing polyaniline involves reacting aniline with stoichiometric amounts of ammonium persulfate in the presence of p-toluene sulfonic acid (TSA). The reaction produces ammonium sulfate as a by-product. The TSA anion is the dopant rendering the polymer conductive. The sulfate anion by-product competes with TSA for the polyaniline protonated sites. Excess TSA is usually used in order to minimize sulfate doping of the polymer. This excess TSA has to be removed after the reaction is complete. Thus, the chemical synthesis of polyaniline produces a rather large quantity of undesirable ammonium sulfate by-product and requires excess TSA.

Others have attempted to produce polyaniline enzymatically; however, their procedures have yielded a mixture of low molecular weight oligomers and azo-linked species. Aizawa et al, in "Enzymatic Synthesis of Polyaniline Film Using a Copper-Containing Oxidoreductase: Bilirubin Oxidase", *Journal of Biotechnology*, 14, 301 (1990), discuss enzymatic polymerization of aniline wherein the resulting aniline polymer contains symmetric head-to-head (N-N) coupling bonds. Mann and Sanders, in "Studies in Peroxidase Action 1-The Oxidation. of Aniline" *Proceedings of the Royal Society*, 119 pp 47–60 (1935) also oxidized aniline enzymatically using a solution of aniline in dilute acetic acid at a pH of 4.5 with a peroxidase system. They describe their product as a mixture of related substances: 2,5-dianilino-para-benzoquinone imide-anil, indulene, pseudomauveine and ungreenable aniline black. On page 49 of this reference, it is depicted that ungreenable aniline black was formed by the further oxidation of quinone-anil-(4(4-aminoanilino)anil) through emeraldine and nigraniline forms of polyaniline having only eight aniline repeat units. All of these products are soluble in a large variety of solvents, which suggests that they are of low molecular weight.

The invention described herein resolves many of the disadvantages associated with chemical and enzymatic synthesis of polyaniline.

SUMMARY OF THE INVENTION

The present invention relates to a process of forming polyaniline having greater than 8 aniline monomer repeating units. Homopolymers and copolymers of aniline monomers can be formed by the process of this invention. The process comprises polymerizing one or more substituted or unsubstituted aniline monomers in the presence of an oxidizing agent and an effective acidifying agent at an effective pH in a solvent; wherein said oxidizing agent comprises an enzyme and an electron acceptor, said enzyme being oxidizable by said electron acceptor under process conditions.

In this process an enzyme is employed to catalyze the synthesis of polyaniline from aniline monomer and a electron acceptor for the enzyme. The electron acceptor oxidizes the enzyme which in turn oxidizes the aniline to a precursor form which polymerizes readily to polyaniline.

The polyanilines produced by the process of this invention are generally electrically conductive. As used herein electrically conductive in reference to polyaniline means having a conductivity of at least about $10^{-6}$ S/cm as measured by the four-in-line probe method. Highly conductive polyaniline(at least about 0.5 S/cm as measured by the four-in-line probe method) can be produced by the present process.

The present invention presents numerous advantages over other processes for preparing polyaniline. In comparison to other enzymatic methods, the present process provides high molecular weight polyaniline whereas other attempts to synthesize polyaniline enzymatically have produced only short oligomers of eight or less monomeric repeating units along the polymer backbone.

The present process also presents advantages over chemical methods for making polyaniline. The chemical method as discussed above generates a large amount of undesirable ammonium sulfate by-product. The ammonium persulfate oxidizes the aniline; however it generates a sulfate anion which competes with an acidifying agent, such as toluene sulfonic acid for doping of the polymer. In the present enzymatic process, there is no anion generated by the oxidizing agent to compete with the acidifying agent; therein an excess acidifying agent is not required. Also undesirable side-products like ammonium sulfate are not generated. In general, the enzymatic process will produce a less toxic by-product or one that is more easily separated and discarded than the by-product of the chemical process. In the present invention, when aniline is oxidized in water by hydrogen peroxide, in the presence of the enzyme, the products formed are substantially polyaniline and water.

In addition to the above advantages, the enzymatic process of this invention produces an electrically conductive polymer from a one-step process.

The advantages and further embodiments will become more apparent from the detailed description and examples provided herein.

DETAILED DESCRIPTION OF THE INVENTION

In the enzymatic synthesis of polyaniline of this invention, aniline monomer, an oxidizing agent, which comprises an enzyme and an electron acceptor, and an acidifying agent are reacted at an effective pH in a solvent.

The aniline component is selected from one or more substituted or unsubstituted aniline monomers. Useful anilines may vary widely. Illustrative of such monomers are unsubstituted and substituted anilines of Formula I:

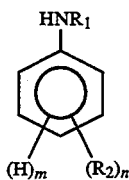

Formula I wherein:
n is an integer from 0 to 4,
m is an integer from 1 to 5 with the proviso that the sum of n and m is equal to 5 and that at least one position on the aniline ring is a moiety which allows oxidative coupling at that position.

$R_1$ is a hydrogen or a permissible $R_2$ substituent.

$R_2$ is the same or different at each occurrence and is selected from the group consisting of alkyl, alkenyl, alkoxy, cycloalkyl, cycloalkenyl, alkanoyl, alkylthio, aryloxy, alkylthioalkyl, alkylaryl, arylalkyl, amino, alkylamino, dialkylamino, aryl, alkylsulfinyl, aryloxyalkyl, alkylsulfinylalkyl, alkoxyalkyl, alkylsulfonyl, aryl, arylthio, alkylsulfonylalkyl, arylsulfinyl, alkoxycarbonyl, arylsulfonyl, carboxylic acid, hydroxy, halogen, cyano, sulfonic acid, nitro, mercapto, alkylsilane or alkyl substituted with one or more sulfonic acid, carboxylic acid, halo, nitro, mercapto, cyano or epoxy moieties; or any two $R_2$ groups together may form an alkylene or alkenylene chain completing a 3, 4, 5, 6 or 7 membered aromatic or alicyclic ring, which ring may optionally include one or more divalent nitrogen, sulfur, sulfonyl, ester, carbonyl, sulfonyl, or oxygen atoms; or $R_2$ is an aliphatic moiety having repeat units of the formula:

—(OCH$_2$CH$_2$)$_q$O—, or —(OCH$_2$CH(CH$_3$))$_q$O— q is a positive whole number. A moiety which allows oxidative coupling is any moiety that does not hinder the head-to-tail coupling of the monomers in forming polyaniline. An example of such a moiety is hydrogen or deuterium.

Preferably, the aniline monomer is substituted at the ortho- or para-position with a moiety which allows oxidative coupling of the monomers. In more preferred embodiments, the aniline monomer is substituted at the para-position with a moiety which allows oxidative coupling of the monomers. In alternatively preferred embodiments, the aniline monomer is substituted at the ortho- or para-position with a hydrogen (or a deuterium). In particularly preferred embodiments, the aniline monomer is substituted at the para-position with a hydrogen.

Exemplary of useful $R_1$ groups are hydrogen, methyl, ethyl, isopropyl, butyl, isobutyl, hexyl, octyl and the like.

Illustrative of useful $R_2$ groups are hydrogen, alkyl such as methyl, ethyl, octyl, nonyl, tert-butyl, neopentyl, isopropyl, sec-butyl, dodecyl and the like, alkenyl such as 1-propenyl, 1-butenyl, 1-pentenyl, 1-hexenyl, 1-heptenyl, 1-octenyl and the like; alkoxy such as propoxy, butoxy, methoxy, isopropoxy, pentoxy, nonoxy, ethoxy, octoxy, and the like; cycloalkenyl such as cyclohexenyl, cyclopentenyl and the like; alkanoyl such as butanoyl, pentanoyl, octanoyl, ethanoyl, propanoyl and the like; alkylsulfinyl, alkylsulfonyl, arylsulfinyl alkylthio, arylthio, arylsulfonyl, and the like, such as butylthio, neopentylthio, methylsulfinyl, benzylsulfinyl, phenylsulfinyl, propylthio, octylthio, nonylsulfonyl, octylsulfonyl, methylthio, isopropylthio, phenylsulfonyl, methylsulfonyl, nonylthio, phenylthio, ethylthio, benzylthio, phenethylthio, sec-butylthio, naphthylthio and the like; alkoxycarbonyl such as methoxycarbonyl, ethoxycarbonyl, butoxycarbonyl and the like; cycloalkyl such as cyclohexyl, cyclopentyl, cyclooctyl, cycloheptyl and the like; alkoxyalkyl such as methoxymethylene, ethoxymethyl, butoxymethyl, propoxyethyl, pentoxybutyl and the like; aryloxyalkyl and aryloxyaryl such as phenoxyphenyl, phenoxymethylene and the like; and various substituted alkyl and aryl groups such as 1-hydroxybutyl, 1-aminobutyl, 1-hydroxypropyl, 1-hydroxypentyl, 1-hydroxyoctyl, 1-hydroxyethyl, 2-nitro-ethyl, trifluoromethyl, 3,4-epoxybutyl, cyanomethyl, 3-chloropropyl, 4-nitrophenyl, 3-cyanophenyl, and the like; sulfonic acid terminated alkyl and aryl groups and carboxylic acid terminated alkyl and aryl groups such as ethylsulfonic acid, propylsulfonic acid, butylsulfonic acid, phenylsulfonic acid, and the corresponding carboxylic acids.

Also illustrative of useful $R_2$ groups are divalent moieties formed from any two $R_2$ groups such as moieties of the formula:

(CH$_2$)$_d$(CH$_2$)$_a$ wherein a is an integer from about 3 to about 7, as for example (CH$_2$)4, (CH$_2$)3 and (CH$_2$)5, or such moieties which optionally include heteroatoms of oxygen, nitrogen, ester, sulfonyl, carbonyl, and/or sulfur such as —CH$_2$SCH$_2$— —CH$_2$NHCH$_2$—, —SCH$_2$NCH$_2$—, —OCH$_2$—S—CH$_2$, CH$_2$S(O$_2$)CH$_2$—, —CH$_2$—O—CH$_2$— to form heterocyclic amino compounds such as tetrahydronaphthylamine, dihydrobenzopyrroleamine, benzofuranamine, dihydrobenzopyranamine, dihydrobenzofuranamine, dihydrobenzoparoxazineamine, dihydrobenzoparadiazineamine, dihydrobenzotetrazoleamine, dihydrobenzothiazineamine, benzothiopyranamine, dihydrobenzoxazoleamine and the like. Exemplary of useful $R_2$ groups are divalent alkenylene chains containing 1 to about 3 unsaturated bonds such as divalent 1,3-butadiene and like moieties which may also include one or more oxygen, nitrogen, sulfonyl, carbonyl, ester, and/or sulfur which form such compounds as benzodiazineamine, benzodiazoleamine, benzotriazepineamine, benzoimidazolylamine, benzoxazoleamine, benzoixazoleamine, benzoxazolylamine, benzotriazineamine, benzoxazineamine, naphthaleneamine, benzopyranamine, benzothiazineamine, anthraceneamine, aminobenzothiopyran, aminobenzodiazine, benzethiopyrone, aminocoumarin, benzothiophene, benzothiodiazoleamine, and the like.

Preferred embodiments of the invention are directed to aniline monomers of Formula I wherein $R_1$ is hydrogen or an $R_2$ substituent, $R_2$ being selected from hydrogen, hydroxy, halogen, cyano, nitro, mercapto, sulfonic acid, carboxylic acid; and a hydrocarbon-containing substituent selected from alkyl, alkanoyl, alkoxy, alkenyl, cyclo-alkenyl, aryl, aryloxy, aryloyl, alkylaryl or alkyl substituted with one or more of halogen, cyano, nitro, mercapto, sulfonic acid and carboxylic acid; said hydrocarbon substituent having 1 to 20 carbons. Further preferred embodiments are directed to aniline monomers of Formula I wherein $R_1$ is hydrogen or an $R_2$ substituent, $R_2$ being selected from hydrogen, hydroxy, halogen, cyano, nitro, mercapto, sulfonic acid, carboxylic acid, and a hydrocarbon-containing substituent selected from alkyl, alkanoyl, alkoxy, alkenyl, cyclo-alkenyl, aryl, aryloxy, aryloyl, alkylaryl or alkyl substituent with one or more of halogen, cyano, nitro, mercapto, sulfonic acid and carboxylic acid; said hydrocarbon substituent having 1 to 12 carbons. More preferred embodiments are directed to aniline monomers of Formula I wherein $R_1$ is hydrogen or an $R_2$ substituent, $R_2$ being selected from hydrogen, hydroxy, halogen, cyano, nitro, mercapto, sulfonic acid, carboxylic acid, and a hydrocarbon-containing substituent selected from alkyl, alkanoyl, alkoxy, alkenyl, cyclo-alkenyl, aryl, aryloxy, aryloyl, alkylaryl or alkyl substituted with one or more of halogen, cyano, nitro, mercapto, sulfonic acid and carboxylic acid; said hydrocarbon substituted having 1 to 8 carbons. Particularly preferred embodiments are directed to aniline monomers of Formula I wherein $R_1$ is a hydrogen or alkyl having 1 to 8 carbons and $R_2$ is selected from hydrogen, hydroxy, halogen, cyano, carboxylic acid, sulfonic acid; and a hydrocarbon-containing substituent selected from alkyl, alkanoyl, alkoxy, alkenyl, alkyl, phenyl, alkyphenoxy, alkyl phenoyl and alkyl substituted with halogen, cyano, mercapto, carboxylic acid and sulfonic acid, said hydrocarbon substituent having 1 to 8 carbons. More particularly preferred embodiments are directed to aniline monomers of Formula I wherein $R_1$ is hydrogen or an alkyl having 1 to 4 carbons and $R_2$ is selected from a hydrogen, hydroxy, halogen, cyano, mercapto, carboxylic acid, sulfonic acid and an alkyl, alkoxy, alkanoyl; said alkyl having 1 to 6 carbons. In the most preferred embodiments of this invention, the aniline monomer is unsubstituted aniline.

The following listing of substituted and unsubstituted anilines are illustrative of those which can be used in the practice of this invention for preparing polymers and copolymers.

| | |
|---|---|
| Aniline | 2-Acetylaniline |
| 2-Cyclohexylaniline | 2,5-Dimethylaniline |
| o-Toluidine | 2,3-Dimethylaniline |
| m-Toluidine | 2,5-Dibutylaniline |
| o-Ethoxyaniline | o-Cyanoaniline |
| m-Butylaniline | 2-Thiomethylaniline |
| m-Hexylaniline | 2,5-Dichloroaniline |
| m-Octylaniline | 3-(n-Butanesulfonic acid) aniline |
| 2-Bromoaniline | 3-Propoxymethylaniline |
| 3-Bromoaniline | 3-Acetamidoaniline |
| 5-Chloro-2-methoxy-aniline | 3-Phenoxyaniline |
| N-Methylaniline | 2-(Dimethylamino)aniline |
| 2-Ethylthioaniline | N-Carbonylaniline |
| 2-Methylthiomethylaniline | |

The oxidizing agent component of this invention comprises an enzyme and an electron acceptor which is capable of oxidizing the enzyme. The enzyme is selected based on its ability to oxidize aniline to a precursor form which readily polymerizes to polyaniline. An effective enzyme for use in the process of this invention is an enzyme capable of oxidizing aniline at an effective pH. Generally, the enzyme must retain its activity in an acidic environment for time sufficient to oxidize the aniline monomer. The source of enzyme is not critical. The enzyme can be natural or synthetic. Synthetic refers to enzymes produced by recombinant DNA methods. Synthetic enzymes may be advantageous if they are designed to work under reaction conditions specific to the enzymatic synthesis of polyaniline. In preferred embodiments of the invention, an effective enzyme is a peroxidase or oxidase. In more preferred embodiments of the invention, a peroxidase enzyme is used. In particularly preferred embodiments, the enzyme is horseradish peroxidase. Any electron acceptor known to be useful to oxidize the enzyme may be used. Preferably, a hydroperoxide is used as an electron acceptor with a peroxidase and oxygen or an oxygen containing gas is used with an oxidase. Any peroxide known to be useful as an electron acceptor with a peroxidase can be employed in the practice of the invention. Illustrative of such peroxides are hydrogen peroxide, alkyl hydroperoxides; such as methyl hydroperoxide and ethyl hydroperoxide, aromatic peroxides, for example cumen hydroperoxide and peroxy acids. In additionally preferred embodiments, when the electron acceptor oxidizes the enzyme, the electron acceptor's reduced form is a component of the solvent. For example, hydrogen peroxide is converted to water upon oxidizing the enzyme. Therein, when the reaction is conducted in water, using hydrogen peroxide as the electron acceptor, the need for a process step to separate by-product formed by the reduction of the electron acceptor is eliminated. Similarly, using methyl hydroperoxide when conducting the reaction in methanol eliminates the need for a separation step since the by-product of the reduced methyl hydroperoxide is methanol.

The enzymatic reaction is conducted in the presence of an acidifying agent. An effective acidifying agent is able to protonate the aniline monomer. The "effective" acidifying agent (or proton donor) should have a pKa which is less than the pKa of the aniline being polymerized. Without an effective acidifying agent, less aniline monomer is protonated; therein, less protonated monomer is available for polymerization and the yield of relatively high molecular weight polyaniline is decreased accordingly. Without the effective acidifying agent, the product of the reaction is short oligomers with possibly only 8 or less aniline monomeric units. Preferably, the acidifying agent also serves as a dopant. A dopant is any species which provides electrical conductivity to the polymer product. As a dopant, the acidifying agent generally protonates the backbone of conjugated. polymers and creates charge carriers along the polymer backbone, resulting in an electrically conductive material.

For aniline, which has a pKa of approximately 4.7, an effective acidifying agent should have a pKa lower than 4.7. Preferably the pKa (acidifying agent) is less than or equal to 3.5. In particularly preferred embodiments the acidifying agent has a pKa equal to or less than 3.0. The above requirements are general guidelines for enzymatic polymerization of aniline. The pKa of the acidifying agent can vary with the pKa of the particular aniline employed. Substituents on the monomer can increase or decrease the pKa of the monomer such that the requisite pKa of the acidifying agent will vary accordingly. In general, electron donating groups as substituents on the aniline will increase the pKa of the monomer, allowing for weaker acids to be used as acidifying agents. Alternatively, electron-withdrawing groups as substituents on the aniline will decrease the pKa of the monomer necessitating the use of stronger acids.

Any inorganic or organic acid having a pKa less than the pKa of the aniline monomer can be employed as an acidifying agent in the reaction. Illustrative of acids for use with aniline or aniline monomers with a pKa greater than that of aniline are HCl, HNO$_3$, H$_2$SO$_4$, HBF$_4$, $C_{12}H_{25}C_6H_4SO_3H$, $CH_3C_6H_5SO_3H$, $C_6H_5SO_3H$, $CH_3SO_3H$, $CF_3SO_3H$, $CF_3COOH$ and $CCl_3COOH$. Inorganic and organic phosphoric acids, phosphoric acids, sulfinic acids and the like can also be used. Such acids are described in PCT International Publication No. WO 89/01694(published Feb. 23, 1989), which is incorporated herein by reference. Those acids with lower pKa's are preferred since less acid is used (at a chosen pH).

The enzymatic synthesis of this invention can be carried out in a variety of solvents known in the art of enzymatic synthesis, including water, organic solvents or a mixture thereof. It is proposed that the choice of solvent or solvent mixture can affect the reaction as well as products formed therefrom (as far as molecular weight and, corresponding, conductivity). By employing an organic solvent, one can increase the monomer concentration in the solvent (to a monomer concentration greater than in water). The higher concentration of monomer in the reaction mixture should provide more available monomer for polymerization, thus forming a polymer of increased molecular weight.

Organic solvents which may be suitable as solvents or suitable for use in solvent/water mixtures include acetone; alcohols, such as methanol, ethanol, propanol and butanol; pyrrolidinones, for example N-methyl,2-pyrrolidinone; acetonitrile and tetrohydrofuran. Preferably, the organic solvent/water mixtures comprise at least about 0.5% water. More preferably, the organic solvent/water mixtures comprise at least about 5% water. In further preferred embodiments the organic solvent/water mixtures comprise from at least about 5 to about 50% water. In the most preferred embodiment, the solvent medium is 100% water The amounts of the various components in the reaction mixture may vary widely. For the acidifying agent, the amount used in the reaction mixture is determined by the choice of pH for the reaction. The acidifying agent is titrated into this mixture to the selected pH of the reaction.

Generally, the monomer concentration in the reaction mixture should be sufficient to form a solution of reaction mixture such that the monomer remains dispersed in the solution prior to the oxidative coupling of the monomers to the polymer product and the monomer is readily exposed to the oxidizing agent and acidifying agent for the oxidative coupling. Preferably, the monomer concentration is such that the monomer is dispersed in a substantially uniform manner throughout the reaction mixture. In further preferred embodiments, the reaction mixture is saturated with the monomer, which is substantially uniformly dispersed throughout the reaction mixture. The molar concentration of monomer is at least about 0.001M and in many instances ranges from about 0.001M to about 1M. Preferably, the concentration of monomer ranges from about 0.01M to about 1M. More preferably, the concentration of monomer ranges from about 0.01M to about 0.7M. In further preferred embodiments the concentration of monomer ranges from about 0.01M to about 0.5M. In further preferred embodiments the concentration of monomer ranges from about 0.05M to about 0.5M, with the range of choice being about 0.1M to about 0.4M.

The amount of enzyme in the reaction should be sufficient to couple enough of the aniline monomer to form a polymer product of a desired molecular weight. The concentration of enzyme is at least about 0.1 units/ml. Units/ml is a conventional measurement of enzyme concentration. The concentration of the enzyme is measured in activity units per milliliter of reaction medium wherein one unit of enzyme will act upon one micromole of a compound to transform that compound to 1.0 micromole of product in a set time at a specific pH and temperature (usually within one minute and at ambient temperature). For example, in the case of the horseradish peroxidase used in the examples to illustrate several of the embodiments of this invention, one unit of activity (ppu) will form 1.0 milligram of purpurogallin from pyrogallol in twenty seconds at pH=6.0 at 20° C. In preferred embodiments of this invention, the concentration of enzyme per milliliter of reaction medium ranges from about 0.1 units/ml to about 10,000 units/ml. In more preferred embodiments, the concentration of enzyme is about 1 to 5,000 units/ml. In particularly preferred embodiments, the concentration of enzyme is about 10 to 1,000 units/ml. In further preferred embodiments, the concentration of enzyme is about 50 to 5000 units/ml. The amount of enzyme used should not exceed the amount of enzyme required to make the polyaniline of the desired weight.

The amount of electron acceptor determines the form of the polyaniline produced (i.e. the ratio of imine to amine bonds in the polyaniline). Preferably, the molar ratio of electron acceptor to monomer is at least about 1:1. More preferably, the electron acceptor/monomer ratio ranges from at least 1:1 to about 4:1. In particularly preferred embodiments, the electron acceptor/monomer ratio ranges from about 1:1 to 3:1, with the ratio of choice ranging from about 1.5:1 to 2:1.

The amount of solvent will vary immensely. The amount of solvent need only form a vehicle in which the components of the reaction can be easily mixed and dispersed throughout. Preferably, when combined with the other components of the reaction mixture, the amount of solvent is sufficient to form a uniform dispersion of the reactants.

As noted, the enzymatic reaction of this invention is carried out in an acidic environment. Generally, the pH of the reaction mixture is sufficiently acidic to cause the protonation of the aniline monomer. At an effective pH, the pH of the reaction mixture is less than the pKa of the aniline monomer in the reaction mixture. Preferably, an effective pH creates an environment wherein at least 70% of the aniline monomer is in its protonated form when it is a monomer dispersed in the reaction mixture. In more preferred embodiments, the pH is selected such that at least about 80% percent of the aniline monomer in the mixture is protonated. In further preferred embodiments, the pH causes at least about 90% of the aniline monomer to be protonated. In particularly preferred embodiments, the pH is selected such that at least about 95% of the aniline is protonated. In more particularly preferred embodiments, the pH is selected such that at least about 98% of the aniline monomer is protonated.

The actual pH of the reaction mixture is governed by the amount of acidifying agent and the pKa of the acidifying agent. Generally, for unsubstituted aniline, the pH is less than about 4.5 for the oxidative coupling of aniline. Preferably, the pH is greater than about 1 and less than about 4.5. In further preferred embodiments, the pH is equal to or greater than about 2.0 and less than about 4.0. In particularly preferred embodiments, the pH is greater than or equal to 2.5 and less than about 3.5. For substituted anilines, the preferred pH should be below the pKa of the substituted aniline monomer(i.e. if substituted aniline has a pKa=5, the pH for the reaction should be less than 5).

The enzymatic reaction can be carried out at a wide variety of temperatures. Preferably, the enzymatic reaction is carried out at a temperature of at least about 0° C. Additional preferred temperatures are listed below with the more preferred ranges are listed last.

PREFERRED TEMPERATURE RANGES FOR THE REACTION 1. 0°–100° C.
2. 0°–90° C.
3. 0°–75° C.
4. 0°–50° C.
5. 0°–25° C.
6. 0°–10° C.

The order of addition of the components of the reaction is not critical. The components can be added all at once or separately. Preferably, the enzyme is added last to preserve the maximum available activity of the enzyme in the acidic environment. The enzyme can also be added all at once or in a stepwise manner. The electron acceptor can be added all at once or in a stepwise manner such that the concentration of the electron acceptor in the reaction mixture does not reach a level at which the enzyme becomes deactivated.

The polyanilines produced by this process of this invention result from head-to-tail coupling of aniline monomers. The polyanilines formed by the process of this invention have more than 8 monomer units in the backbone of this polymer chain. Preferably, the number of monomer units along the backbone of the polymer chain is at least about 10. More preferably, the number of monomer units is at least about 20. In further preferred embodiments, the number of monomer units is at least about 50. In particularly preferred embodiments, the number of monomer units is at least about 75. In more particularly preferred embodiments, the number of monomer units is at least about 150. In the most preferred embodiment, the number of monomer units is at least about 200.

One application of polyanilines is their use in forming electrically conductive films. Therein, polyaniline which are of "film-forming molecular weight" are particularly useful. As used herein, "film forming molecular weight: generally means number average molecular weights which exceed about 15,000. The molecular weight of the substituted or unsubstituted polyaniline at which the polymer will be film-forming may vary widely, depending on a number of factors including the number of repeat units, and the number of substituents and the substituent. In general, substituted and unsubstituted polyanilines will be of film-forming molecular weight when the number of monomer repeat units is at least about 150.

Illustrative of the polyanilines prepared by the practice of this invention are those of Formulas II to V:

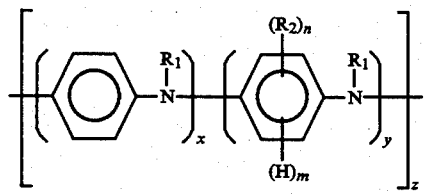

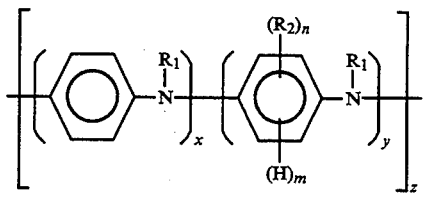

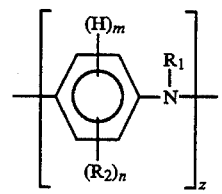

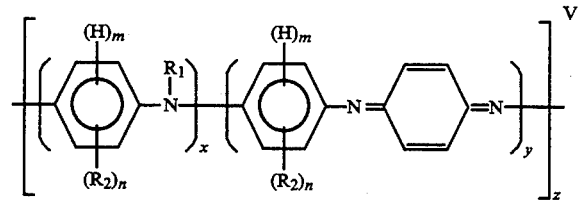

wherein $R_1$ and $R_2$ are as described above;

y is an integer equal to or greater than 0;

X is an integer equal to or greater than about 0, with the proviso that at least x or y is greater than 0 and that when x and y are greater than 0, the ratio of x to y is greater than or equal to 0.5; and z is an integer selected such that the number of aniline monomer units along the polymer backbone is greater than 8.

Preferred for use in the practice of this invention are polyanilines of the above Formulas II to V in which:

n is an integer from 0 to 2;

m is an integer from 3 to 4, with the proviso that the sum of n and m is equal to 4;

$R_1$ is a hydrogen or a methyl;

$R_2$ is an alkyl or an alkoxy having from 1 to about carbon atoms or an alkyl having from 1 to about 20 carbon atoms substituted with carboxylic acid or sulfonic acid substituents;

x is an integer equal to or greater than 1;

y is equal to or greater than 0, with the proviso that when y is greater than 0, the ratio of x to y is greater than about 2; and z is an integer selected such the number of monomer units along the polymer backbone is equal to or greater than about 20.

Particularly preferred embodiments are directed to polyanilines of the above Formulas II to V in which:

n is an integer from 0 to 1;

m is an integer from 4 to 5, with the proviso that the sum of n and m is equal to 5;

$R_1$ is a hydrogen $R_2$ is an alkyl or an alkoxy from 1 to about 4 carbon atoms;

x is an integer equal to or greater than 4;

y is equal to or greater than 1, with the proviso that the ratio of x to y is greater than about 2; and z is an integer selected such the number of monomer units along the polymer backbone is equal to or greater than about 30.

In the most preferred embodiments of this invention, the polyaniline is derived from unsubstituted aniline.

The polyanilines produced by the enzymatic method of this invention have varied conductivities dependent on the type and amount of acidifying agents and electron acceptors used for the synthesis. As discussed above, the acidifying agents may act as chemical dopants by creating charge carriers along the polymer backbone. Since the electron acceptor effects the number of imine bonds in the polymer backbone, it also effects the degree of conjugation along the polymer backbone. Preferably, the electron acceptor creates a polymer having about 50% of the nitrogens along the polymer backbone in the form of an imine bond.

Generally, the polyanilines produced by the one-step enzymatic process of this invention possess an electrical conductivity of at least about $10^{-6}$ S/cm. Preferably, the electrical conductivity is at least about $10^{-3}$ S/cm. More preferably, the conductivity is at least about $10^{-1}$ S/cm. In further preferred embodiments, the conductivity is at least about $3 \times 10^{-1}$ S/cm. In particularly preferred embodiments, the conductivity is at least about $5 \times 10^{-1}$ S/cm. In additionally preferred embodiments, the electrical conductivity of polyaniline is at least about 1 S/cm. In the most preferred embodiment, the conductivity is at least about 2 S/cm. It is noted that the higher levels of conductivity (above $5 \times 10^{-1}$ S/cm) can be obtained by subjecting the polyaniline to an post treatment doping process. Methods of doping polymers as well as the dopants for use therein are described in U.S. Pat. Nos. 4,222,903; 4,204,216; 4,517,116; 4,521,589; 4,711,742 and 4,789,748 which are incorporated herein by reference.

Nonconductive polyaniline may also be produced by treating the enzymatically produced polyaniline with a base. The polyaniline produced by the enzyme method can be washed with a base solution (e.g. ammonium hydroxide in methanol or ethanol) to render the material non-conductive. If desired the neutral or non-conductive polyaniline can also be redoped accordingly to conventional doping procedures discussed above.

Another aspect of this invention relates to compositions comprising one or more doped electrically conductive polyanilines of this invention, and one or more thermoplastic polymers. The proportion of polyaniline to thermoplastic polymer is not critical and may vary widely, depending on the use of the composition. For example, for those uses which require the composite having higher conductivities, i.e., up to or greater than about $10^{-1}$ ohm$^{-1}$/cm$^{-1}$, the amount of electrically conductive polyaniline will tend to be relatively high, as for example up to and greater than about 5 weight percent, based on the total weight of the composition. Conversely, for those uses in which lower conductivities are required, i.e., down to or less than about $10^{-6}$ ohm/1 cm$^{-1}$, the amount of electrically conductive polyaniline will tend to be relatively low, down to or less than about 5 weight percent based on the total weight of the composition. In the preferred embodiments of the invention, the amount of electrically conductive polyaniline is from about 5 to about 40 weight percent based on the total weight of the composition, and in the particularly preferred embodiments of the invention the amount of conductive polyaniline is from about 5 to about 30 weight percent on the aforementioned basis. Amongst these particularly preferred embodiments most preferred are those embodiments in which the composition comprises from about 5 to about 20 weight percent of the electrically conductive polyaniline based on the total weight of the composition.

Thermoplastic polymers for use in the formulation of the composition of the invention may vary widely. Illustrative of such polymers are polyesters such as poly(glycolic acid), poly(ethylene succinate), poly(ethylene adipate), poly(tetramethylene adipate), poly(ethylene azelate), poly(ethylene sebacate), poly(decamethylene adipate), poly(decamethylene sebacate), poly(2,2-dimethylpropiolactone), poly(pivaloyl lactone), poly(para-hydroxybenzoate), poly(ethylene oxybenzoate), poly(ethylene isophthalate), poly(ethylene terephthalate), poly(decamethylene terephthalate), poly(hexamethylene terephthalate), poly(1,4-cyclohexane dimethylene terephthalate), poly (ethylene-1,5-naphthalate), poly (ethylene-2,6-naphathalate), poly (1,4-cyclohexylided dimethylene-teraphthalate) and the like; polyamides such as poly(4-aminobutyric acid) (nylon 4), poly(6-aminohexanoic acid) (nylon 6), poly(7aminoheptanoic acid) (nylon 7), poly(8-aminooctanoic acid) (nylon 8), poly(9-amino-nonanoic acid) (nylo 9), poly(10-aminodecanoic acid) (nylon 10), poly(11-aminoundecanoic acid) (nylon 11), poly(12-aminododecanoic acid) (nylon 12), poly(hexamethylene adipamide) (nylon 6,6), poly(heptamethylene pimelamide) (nylon 7,7), poly(octamethylene suberamide) (nylon 8,8), poly(hexamethylene sebacamide), (nylon 6,10), poly(nonamethylene azelamide) (nylon 9,9), poly(decamethylene azelamide) (nylon 10,9), poly(decamethylene sebacalide) (nylon 10,10), poly[bis (4-aminocyclohexyl)methane-1,10-decanedicarboxamide] (Quiana) (trans), poly(m-xylene adipamide), poly(p-xylene sebacamide) , poly(2,2,2-trimethylhexamethylene texephthalamide), poly(piperazine sebacamide), poly(metaphenylene isophthalamide) (Nomex), poly(p-phenylene terephthalamide) (Kevlar), and the like; polycarbonates such as poly[methane bis(4-phenyl)carbonate], poly[1,1-ethane bis(4-phenyl)carbonate] poly[2,2-propane bis(4-phenyl)carbonate], poly[1,1-butane bis(4-phenyl)carbonate], poly[1,1-(2methyl propane)-bis(4-phenyl carbonate], poly[2,2-butane bis(4-phenyl)-carbonate], poly[2,2-pentane bis(4-phenyl)carbonate], poly[4,4-heptane bis(4-phenyl)carbonate], poly[1,1-(1-phenylethane)bis(4-phenyl)carbonate], poly[diphenylmethane bis(4-phenyl)carbonate], poly[1,1-cyclopentance bis(4-phenyl)carbonate], poly[1,1-cyclohexane bis(4-phenyl)carbonate], poly[thio bis-(4-phenyl)carbonate], poly[2,2-propane bis-4-(2-methyl phenyl)carbonate], poly[2,2-propane bis-4-(2-chlorophenyl)carbonate], poly[2,2-propane bis-4-(2,6-dichlorophenyl)carbonate], poly[2,2-propane bis-4-(2,6-dibromophenyl)carbonate], poly[1,1-cyclohexane bis-(2,6-dichlorophenyl)carbonate], and the like; polymers derived from the polymerization of α,β-unsaturated monomers such as polyethylene, polypropylene, poly(1-butene), poly(3-methyl-1-butene), poly(1-pentene), poly(4-methyl-1-pentene), poly(1-hexene), poly(5-methyl-1-hexene), poly(1-octadecene), polyisobutylene, 1,2-poly(1,3-butadiene) (iso), 1,2-poly(1,3-butadiene) (syndio), polystyrene, poly(a-methylstyrene), poly(2-methyl-styrene), poly(4-methylstyrene), poly(4-methoxystyrene), poly(4-phenylstyrene), poly(3-phenyl-1-propene), poly(2-chlorostyrene), poly(4-chlorostyrene), poly(vinyl fluoride), poly(vinyl chloride), poly(vinyl bromide), poly(vinylidene fluoride), poly(vinylidene chloride), poly(tetrafluoroethylene) (Teflon), poly(chlorotrifluoro-ethylene), poly(vinylcyclopentane), poly(vinylcyclohexane), poly(a-vinylnaphthalene), poly(vinyl alcohol), poly(vinyl methyl ether), poly(vinyl ethyl ether), poly(vinyl propyl ether), poly(vinyl isopropyl ether), poly(vinyl butyl ether), poly(vinyl isobutyl ether), poly(vinyl sec.-butyl ether), poly(vinyl tert.-butyl ether), poly(vinyl hexyl ether), poly(vinyl octyl ether), poly(vinyl methyl ketone), poly(methyl isopropenyl ketone), poly(vinyl formate), poly(vinyl acetate), poly(vinyl propionate), poly(vinyl chloroacetate), poly(vinyl trifluoroacetate), poly(vinyl benzoate), poly(2-vinylpyridine), poly(vinylpyrrolidone) poly(vinyl-carbazole), poly(acrylic acid), poly(methyl acrylate), poly(ethyl acrylate), poly(propyl acrylate), poly(isopropyl acrylate), poly(butyl acrylate), poly(isobutyl acrylate), poly(sec.-butyl acrylate), poly(tert.-butyl acrylate), poly(methacrylic acid), poly(methyl methacrylate), poly(ethyl methacrylate), poly(propyl methacrylate), poly(isopropyl methacrylate), poly(butyl methacrylate), poly(isobutyl methacrylate), poly(sec.-butyl methacrylate), poly(tert.-butyl methacrylate), poly(2-ethylbutyl methacrylate), poly(hexyl methacrylate), poly(oxtyl methacrylate), poly(dodecyl methacrylate), poly(octadecyl methacrylate), poly(phenyl methacrylate), poly(benzyl methacrylate), poly(benzyl methacrylate), poly(cyclohexyl methacrylate), poly(methyl chloroacrylate), poly-acrylonitrile, poly-methacrylonitrile, polyacrylamide, poly (N-isopropylacrylamide), and the like; polydienes such as poly(1,3-butadiene) (cis), poly(1,3-butadiene) (trans), poly(1,3-butadiene) (mixt.), poly(1,3-pentadiene) (trans), poly(2-methyl-1,3-butadiene) (cis), poly(2-methyl-1,3-butadiene) (trans), poly(2-methyl-1,3-butadiene) (mixt.), poly(2-tert.-butyl-1,3-butadiene) (cis), poly(2-chloro-1,3-butadiene) (trans), poly(2-chloro-1,3-butadiene) (mixt.) and the like; polyoxides such as poly(methylene oxide), poly(ethylene oxide), poly(tetramethylene oxide), poly(ethylene formal), poly(tetramethylene formal), polyacetaldehyde, poly(propylene oxide), poly(hexene oxide), poly(octene oxide), poly(trans-2-butene oxide), poly(styrene oxide), poly(3-methoxpropylene oxide), poly(3-butoxypropylene oxide), poly(3-hexoxypropylene oxide), poly(3-phenoxypropylene oxide), poly(3-chloropropylene oxide), poly[2,2-bis(chloromethyl), trimethylene-3-oxide] (Penton), poly(2,6-dimethyl-1,4-phenyl oxide) (PPO), poly 2,6-diphenyl-1,4-phenylene oxide) (Texax, P30), and the like; polysulphides such as poly(propylene sulphide), poly(phenylene sulphide) and the like; polysulfones such as poly[4,4'-isopropylidene diphenoxy di(4-phenylene) sulphone], and the like.

The composition of this invention may include various optional components which either fill or form a substrate for the composition. These other components may vary widely and may include any material known for use in a conductive polymer composition. Illustrative of such other components are such materials as graphite, metal conductors, reinforcing fibers, inert fillers, glass beads, clays, other conductive and non-conductive polymers, conductive ceramics, super-conductive ceramics, and the like.

The composition of this invention can be prepared using conventional techniques as for example conventional melt blending techniques. For example, such compositions can be formed by heating a mixture of the various components to a temperature which is equal to or greater than the melting point of at least one of the polymer components to form a molten intimate mixture. Thereafter the mixture can be formed into a desired article. The manner in which the molten mixture is formed is not critical and conventional methods can be employed. For example, the molten mixture can be formed through use of conventional polymer and additive blending means, in which the polymeric components are heated to a temperature equal to or greater than the melting point of at least one of the polymers, and below the degradation temperature of each of the polymers. The desired amount of the optional ingredients in a liquid or powdered form is added to the melted polymers while at the same time vigorously agitating the melt as for example by stirring or irradiating with ultrasound, or added prior to melting and mixing.

In the most preferred embodiment, the components of the initiate mixture can be granulated, and the granulated components mixed dry in a suitable mixer, as for example using ultra-sonication or a tumbler or a Brandbury Mixer, or the like, as uniformly as possible. Thereafter, the composition is heated in an extruder until the polymer components are melted. As described above, the mixture is heated and is thereafter ejected with cooling.

The order of mixing of the various components of the intimate mixture is not critical. Accordingly, the order of addition of the polymers and other optional components to be desired in more detail hereinbelow, to form the initiate mixture can be varied as desired. The electrically conductive polyaniline of the invention, and the composition of this invention can be used for any purpose for which conductive polymers are useful. Examples of articles include conductive polymer coated-housings for sensitive electronic equipment (microprocessors), infrared and microwave absorbing shields, flexible electrical conducting connectors, conductive bearings, brushes and semiconducting photoconductor junctions, antistatic materials for packaging electronic components, carpet fibers, waxes for floors in computer rooms and thin, optically transparent antistatic finishes for CRT screens, aircraft, auto windows and the like.

The following specific examples are presented to more particularly illustrate the invention, and should not be construed as being limitations on the scope and spirit of the invention.

EXAMPLES

In all of the following examples "HRP solution" refers to a solution of Horseradish Peroxidase enzyme in distilled water. Unless specifically stated otherwise, the HRP solution is understood to have an activity of 5000 purpurogallin units/ml and an RZ=3.0.

Except as specifically noted, all chemicals and reagents were the purest commercially available and were used "as received" with no further purification.

All of the Gel Permeation Chromatography (GPC) data were acquired on a Hewlett-Packard 1090 LC using THF (tetrahydrofuran) as the mobile phase. The column was a 300×7.5mm HP PLgel column with a 5μ particle size and a 500 Å pore size. The flow rate was 1 ml/min. The temperature was 40° C. The column was calibrated with polystyrene standards. With these conditions, the run time is 12 minutes. The detector was an HP diode array detector (DAD) set at 300 nm with a bandwidth of 100 nm. All samples were prepared by dissolving approximately 10 mg/ml of the polymer in 1-methyl-2-pyrrolidinone. Injection volumes were varied between 1 and 10 μl to obtain a maximum detection absorbance between 0.1 and 1 AU.

All the conductivity measurements were acquired using the standard four-in-line technique.

Preparation of Conductive Polyaniline by Horseradish Peroxidase

EXAMPLE 1

1.83 ml of aniline (0.02M) was added to 90 ml of distilled water and cooled on an ice bath to 13° C. The pH of this solution was titrated to 3.5 with p-toluene sulfonic acid (tech.). The solution was further cooled to 2° C. and the pH was titrated to 3.0. The reaction was then cooled to 0° C. with a recirculating water bath and stirred rapidly while 3.09 ml of 30% hydrogen peroxide (1.5 equivalents of electron acceptor per mole equivalent of aniline monomer) and 5.0 ml of HRP solution were added. The reaction was stirred at 0° for 60 hours at which point the polymer was collected by vacuum filtration through an 8$\mu$ membrane filter. The filter cake was allowed to suck dry for ten minutes. The polymer was then suspended in a 2% p-toluene sulfonic acid (tech.) solution in distilled water and stirred for 30 minutes. The solution was again filtered and dried as above. The polymer was then suspended in a 15% p-toluene sulfonic acid (tech.) solution in distilled water and stirred for 60 minutes. The polymer was again filtered as above and dried in vacuo in a desiccator for 24 hours. This procedure afforded 1.92 grams of dark green polyaniline with a conductivity >1 siemen/cm. It was shown by GPC that the polymer had a molecular weight >20,000.

EXAMPLE 2

3.66 ml of aniline (0.04M) was dissolved in 100 ml distilled water. The pH of this solution was titrated to 3.0 with p-toluene sulfonic acid. 6.18 ml of 30% hydrogen peroxide (1.5 equivalents) was added to the solution and the apparatus was wrapped in foil to exclude light. 10 ml of HRP solution was added to the un-stirred reaction solution drop-wise over a one hour period. The reaction was allowed to sit undisturbed for 24 hours at which point the polymer was collected by centrifugation and dried in vacuo for 24 hours. This procedure afforded 2.23 grams of dark green polyaniline. The conductivity of the polyaniline, as measured by the four-in-line probe technique, was $7.8 \times 10^{-2}$ siemens/cm. The intrinsic viscosity was 0.341 dL/g as measured in $H_2SO_4$ at 25° C. It was shown by GPC that the polymer had a molecular weight >20,000.

250 mg of the above polymer was suspended in 100 ml of a 1N HCl solution and stirred at room temperature for 30 minutes. The doped polyaniline was collected and dried as above. This doped material had a conductivity (as measured by the standard four-in-line method) of 2.22 siemens/cm. The polyaniline was shown to be insoluble in acetone, chloroform, ethyl acetate, toluene, acetonitrile, and THF. It is soluble in N-methyl-2-pyrrolidinone, DMSO, and concentrated sulfuric acid.

Preparation of Polyaniline using Various Acidifying Agents

EXAMPLE 3

3.66 ml of aniline (0.04M) was dissolved in 100 ml distilled water. The pH of this solution was titrated to 3.0 with concentrated hydrochloric acid. 6.18 ml of 30% hydrogen peroxide (1.5 equivalents) was added to the solution. 10 ml of HRP solution was added to the unstirred reaction solution drop-wise over a one hour period. The reaction was allowed to sit undisturbed for 24 hours at which point the polymer was collected by centrifugation and dried in vacuo for 24 hours. This procedure afforded 400 mg of polyaniline.

EXAMPLE 4

10 ml. of 0.100M aniline solution was added to a 50 ml beaker. The pH of this solution was titrated to 3.0 with concentrated Sulfuric acid. 0.100 ml of 30% hydrogen peroxide (1.0 equivalents) was added to this solution. 0.025 ml of HRP solution was added to the solution with moderate stirring. The reaction proceeded immediately and the polyaniline was collected by filtration after two hours. The polymer was shown to be insoluble in acetone, chloroform, ethyl acetate, toluene, acetonitrile, and THF. The polymer was soluble in N-methyl pyrrolidinone, DMSO, and conc. sulfuric acid. It was shown by GPC that the polymer had a molecular weight >20,000.

For examples 5-7 as well as examples 9-12, the product was verified by GPC and solubility as stated in Example 4.

EXAMPLE 5

As in example 4, except that the acid used was Nitric acid.

EXAMPLE 6

As in example 4, except that the acid used was trifluoro-acetic acid.

EXAMPLE 7

As in example 4, except that the acid used was trichloro-acetic acid.

Polyaniline Prepared with mixed Water/Organic Solvent Systems

EXAMPLE 8

3.66 ml of aniline was dissolved in 100 ml of distilled water. This solution was titrated with p-toluene sulfonic acid to a pH of 3.0. 1.00 ml of this solution was added to a test tube followed by 0.500 ml of acetone. 0.100 ml of 30% hydrogen peroxide was then added to the tube followed by 0.100 ml of Horseradish Peroxidase (5000 ppu/ml) solution. The polymer was collected by centrifugation and dried in vacuo for 24 hours. The polyaniline was observed to form as a dark green precipitate. It was shown by GPC that the polymer had a molecular weight >20,000.

EXAMPLE 9

As in example 8, except that 0.25 ml of N-methyl-2-pyrrolidinone was added instead of acetone.

EXAMPLE 10

As in example 8, except that 0.75 ml of Ethanol was added instead of acetone.

EXAMPLE 11

As in example 8, except that 0.50 ml of acetonitrile was added instead of acetone.

EXAMPLE 12

As in example 8, except that 0.25 ml of tetrahydrofuran was added instead of acetone.

Preparation of Polyaniline at High Temperatures

EXAMPLE 13

1.83 ml of aniline (0.02M) was added to 90 ml of distilled water and warmed on a water bath to 37° C. The pH of this solution was titrated to 3.0 with p-toluene sulfonic acid. The reaction was then stirred rapidly while 3.09 ml of 30% hydrogen peroxide (1.5 equivalents) and 5.0 ml of HRP solution were added. The reaction was stirred at 37° for 24 hours. The polymer was collected by centrifugation and dried in vacuo in a desiccator for 24 hours. This procedure afforded 203 mg of polyaniline. It was shown by GPC that the polymer had a molecular weight >20,000.

EXAMPLE 14

As in example 14, except that the temperature of reaction was 80° C. This produced 163 mg of polyaniline.

Preparation of Polyaniline at pH 3.7

EXAMPLE 15

1.83 ml of aniline (0.02M) was added to 90 ml of distilled water and cooled on a recirculating water bath to 0° C. The pH of this solution was titrated to 3.7 with p-toluene sulfonic acid. The solution was then stirred rapidly while. 3.09 ml of 30% hydrogen peroxide (1.5 equivalents) and 5.0 ml of HRP solution were added. The reaction was stirred at 0° for 24 hours at which point the polymer was collected by vacuum filtration through an 8μ membrane filter. The filter cake was allowed to suck dry for ten minutes. The polymer was then suspended in a 2% p-toluene sulfonic acid solution in distilled water and stirred for 30 minutes. The solution was again filtered and dried as above. The polymer was then suspended in a 15% p-toluene sulfonic acid solution in distilled water and stirred for 60 minutes. The polymer was again filtered as above and dried in vacuo in a desiccator for 24 hours. This procedure afforded. 2.49 grams of dark green polyaniline with a conductivity of 0.84 siemen/cm. It was shown by GPC that the polymer had a molecular weight >20,000.

Preparation of Polyaniline using Lactoperoxidase

EXAMPLE 16

3.66 ml of aniline (0.04M) was dissolved in 100 ml distilled water. The pH of this solution was titrated to 3.0 with p-toluene sulfonic acid. 4.12 ml of 30% hydrogen peroxide (1.0 equivalents) was added to the solution. 100 ml of Lactoperoxidase solution (50 ppu/ml) was then added to this solution drop-wise over the period of one hour. The reaction commenced immediately and is allowed to proceed for 24 hours at which point the polyaniline was collected by centrifugation.

Preparation of Polyailine using a Fungal Peroxidase

EXAMPLE 17

23 μl of aniline was added with stirring to 25 ml of distilled water. The pH of this solution was titrated to 3.0 with concentrated HCl. 15 μl of 30% hydrogen peroxide was added to this solution. An enzyme solution was prepared by dissolving 50 mg of peroxidase from Arthromyces ramosa in 5 ml water. 100 μl of this fungal peroxidase solution was added to the aniline solution and the reaction commenced immediately. The polyaniline was collected by filtration.

Preparation of a Methyl Substituted Polyaniline

EXAMPLE 18

100 ml of 0.1M m-toluidine solution in water was titrated with p-toluene sulfonic acid to a pH of 3.0. 1.03 ml of 30% hydrogen peroxide (1.0 equivalents) was added to the solution. The apparatus was wrapped in foil to exclude light. 10 ml of Horseradish Peroxidase. solution (5000 ppu/ml) was added drop-wise to the reaction mixture. The reaction commenced immediately and was allowed to proceed, undisturbed, for 24 hours. The poly(toluidine) was collected by centrifugation. Yield was 490 mg of black polytoluidine.

250 mg of the polymer was doped with HCl as in example 3. The conductivity, when measured by the standard four-in-line probe technique, was 0.002 siemens/cm.

Comparative Examples

EXAMPLE 19

Aniline was oxidized with Horseradish Peroxidase following the procedures of P. Mann and B. Saunders in "Studies in Peroxidase Action I—The Oxidation of Aniline", *Proc Roy. Soc.,* 119B (1935) p.47.

10.0 g. of aniline was dissolved in 10.0 ml of acetic acid and then diluted to 500 ml with water. The resulting solution had a pH of 4.5. 3.0 ml of 3% hydrogen peroxide was added to this solution followed by 5 ml of Horseradish Peroxidase (5000 ppu/ml). 60 ml of 3% hydrogen peroxide was added to the reaction mixture drop-wise over the course of an hour. The reaction mixture was stirred for 12 hours and the products recovered by filtration. The products from this reaction were isolated following the procedures set fourth by P. Mann and B. Saunders in "Studies in Peroxidase Action. I —The Oxidation of Aniline", *Proc Roy. Soc.,* 119B (1935) p.47. According to this publication, these products are 2,5-dianilino-p-benzoquinone imido-anil, pseudo-mauveine, induline, and "un-greenable" aniline black. All of these products are soluble in organic solvents such as acetone or methylene chloride. Conductive polyaniline is insoluble in these solvents. It was shown by GPC that the products from this reaction had a molecular weight <5,000.

EXAMPLE 20

As in example 2 except that the acid used was acetic acid (pKa=4.75). A large excess of acetic acid was required to titrate tile solution to a pH of 3.0. No reaction occurred upon addition of the enzyme.

EXAMPLE 21

An attempt was made to synthesize polyaniline following the procedure of M. Aizawa et al. in *Journal of Biotechnology,* 14 (1990) 301-310.

1.40 g. of aniline was dissolved in 100 ml of 0.10M potassium phosphate buffer at pH 7.0. 15 ml of this solution was added to a 100 ml flask. A Bilirubin oxidase solution was prepared by dissolving 83 mg of enzyme in 15 ml of cold 0.100M potassium phosphate buffer at pH 7.0. The resulting solution had an activity of 125 biliverdin units/ml. This enzyme solution was added to the stirring aniline solution and air was gently blown over the reaction mixture for 12 hours. At the end of this time the solution was a dark brown color. The brown precipitate was recovered by filtration. It was found to be soluble in methylene chloride and GC/MS analysis indicated that Azobenzene was the major product with some residual aniline remaining.

What is claimed:

1. A process for the enzymatic synthesis of electrically conductive polyaniline comprising:

reacting together one or more aniline monomers selected from the group consisting of substituted and unsubstituted aniline monomers, an oxidizing agent which comprises an enzyme and an electron acceptor, and an effective acidifying agent in an acidic environment having a pH lower than the pKa of said aniline monomers to form an electrically conductive polyaniline having more than 8 monomer units along the backbone of the polymer chain, wherein said acidifying agent has a pKa lower than the pKa of said aniline monomers, said enzyme is a peroxidase, said process is carried out at a temperature of from about 0° C. to about 100° C., said solvent is selected from the group consisting of water, organic solvents or mixtures thereof, and said electrically conductive polyaniline has an electrical conductivity of at least about $10^{-6}$ S/cm as measured by the four-in-line probe technique, wherein the backbone of said electrically conductive polyaniline has the structure:

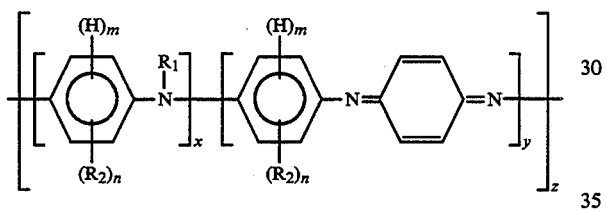

wherein
m is an integer from 1 to 5 with the proviso that the sum of n and m is equal to 5 and that at least one position on the aniline ring is a moiety which allows oxidative coupling at that position;
n is an integer from 0 to 4,
y is an integer equal to or greater than 0;
x is an integer equal to or greater than about 0, with the proviso that at least x or y is greater than 0 and that when x and y are greater than 0, the ratio of x to y is greater than or equal to 0.5;
z is an integer selected such that the number of aniline monomer units along the polymer backbone is greater than 8;
$R_1$ is a hydrogen;
$R_2$ is the same or different at each occurrence and is selected from the group consisting of alkyl, alkenyl, alkoxy, cycloalkyl, cycloakenyl, alkanoyl, alkylthio, aryloxy, alkylthioalkyl, alkylaryl, arylalkyl, amino, alkylamino, dialkylamino, aryl, alkylsulfinyl, aryloxyalkyl, alkylsulfinylalkyl, alkoxyalkyl, alkylsulfonyl, aryl, arylthio, alkylsulfonylalkyl, arylsulfinyl, alkoxycarbonyl, arylsulfonyl, carboxylic acid, hydroxy, halogen, cyano, sulfonic acid, nitro, mercapto, alkylsilane or alkyl substituted with one or more sulfonic acid, carboxylic acid, halo, nitro, mercapto, cyano or epoxy moieties; or any two $R_2$ groups together may form an alkylene or alkenylene chain completing a 3, 4, 5, 6 or 7 membered aromatic or alicyclic ring, which may optionally include one or more divalent nitrogen, sulfur, sulfonyl, ester, carbonyl, sulfonyl, or oxygen atoms; or $R_2$ is an aliphatic moiety having repeat units of the formula:

$$-(OCH_2CH_2)_qO-, \text{ or } -(OCH_2CH(CH_3))_qO-$$

wherein q is a positive whole number.

2. The process of claim 1 wherein the enzyme is horseradish peroxidase.

3. The process of claim 1 wherein said pH is less than about 4.5.

4. The presence of claim 1 wherein said pH is equal to or is less than about 4.0.

5. The process of claim 1 wherein said pH is equal to or less than about 3.5.

6. The process of claim 1 wherein said pH is equal to or less than about 3.0.

7. The process of claim 1 wherein the aniline monomer is substituted at the ortho- or para- position with a hydrogen.

8. The process of claim 1 wherein the aniline is substituted at the para-position with a hydrogen.

9. The process of claim 3 wherein the electron acceptor is a peroxide.

10. The process of claim 3 wherein the electron acceptor is hydrogen peroxide.

11. The process of claim 1 wherein the aniline monomer is selected from anilines of Formula I:

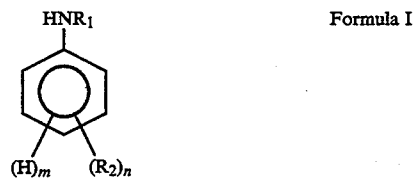

Formula I wherein:
n is an integer from 0 to 4,
m is an integer from 0 to 5 with the proviso that the sum of n and m is equal to 5 and at least one position on the aniline ring is substituted with a moiety which allows oxidative coupling at that position.
$R_1$ is a hydrogen or a permissible $R_2$ substituent;
$R_2$ is the same or different at each occurrence and is selected from the group consisting of alkyl, alkenyl, alkoxy, cycloalkyl, cycloalkenyl, alkanoyl, alkylthio, aryloxy, alkylthioalkyl, alkylaryl, arylalkyl, amino, alkylamino, dialkylamino, aryl, alkylsulfinyl, aryloxyalkyl, alkylsulfinylalkyl, alkoxyalkyl, alkylsulfonyl, aryl, arylthio, alkylsulfonylalkyl, arylsulfinyl, alkoxycarbonyl, arylsulfonyl, carboxylic acid, hydroxy, halogen, cyano, sulfonic acid, nitro, mercapto, alkylsilane or alkyl substituted with one or more sulfonic acid, carboxylic acid, halo, nitro, mercapto, cyano or epoxy moieties; or any two $R_2$ groups together may form an alkylene or alkenylene chain completing a 3, 4, 5, 6 or 7 membered aromatic or alicyclic ring, which ring may optionally include one or more divalent nitrogen, sulfur, sulfonyl, ester, carbonyl, or oxygen atoms; or $R_2$ is an aliphatic moiety having repeat units of the formula:

$$-(OCH_2CH_2)_qO-, \text{ or } -(OCH_2CH(CH_3))_qO-$$

q is a positive whole number.

12. The process of claim 1 wherein the process is carried out at a temperature of from about 0° C. to about 50° C.

13. The process of claim 1 wherein the process is carried out at a temperature of from about 0° C. to about 25° C.

14. The process of claim 1 wherein the process is carried out at a temperature of from about 0° C. to about 10° C.

15. The process of claim 1 wherein the solvent is water.

16. The process of claim 1 wherein the solvent is a water/organic solvent mixture.

17. The process of claim 1 wherein the water/organic solvent mixture comprises at least about 5% water.

18. The polyaniline formed by the process of claim 1.

19. The process of claim 1 wherein the number of monomer units in the backbone of the polymer chain is at least about 10.

20. The process of claim 1 wherein the number of monomer units is at least about 20.

21. The process of claim 1 wherein the number of monomer units is at least about 50.

22. The process of claim 1 wherein the number of monomer units is at least about 75.

23. The process of claim 1 wherein the number of monomer units is at least about 150.

24. The process of claim 1 wherein the polyaniline has an electrical conductivity of at least about $1 \times 10^{-3}$ S/cm as measured by the four-in-line probe technique.

25. The process of claim 1 wherein the polyaniline has an electrical conductivity of at least about $1 \times 10^{-2}$ S/cm as measured by the four-in-line probe technique.

26. The polyaniline formed by process of claim 25.

* * * * *